(12) United States Patent
Kerselaers et al.

(10) Patent No.: US 10,015,604 B2
(45) Date of Patent: Jul. 3, 2018

(54) ELECTROMAGNETIC INDUCTION FIELD COMMUNICATION

(71) Applicant: NXP B.V., Eindhoven (NL)

(72) Inventors: Anthony Kerselaers, Herselt (BE); Liesbeth Gommé, Anderlecht (BE)

(73) Assignee: NXP B.V., Eindhoven (NL)

( * ) Notice: Subject to any disclaimer, the term of this patent is extended or adjusted under 35 U.S.C. 154(b) by 0 days.

(21) Appl. No.: 14/270,013

(22) Filed: May 5, 2014

(65) Prior Publication Data
US 2015/0319545 A1    Nov. 5, 2015

(51) Int. Cl.
| G08C 17/04 | (2006.01) |
| H04B 5/00 | (2006.01) |
| H04R 25/00 | (2006.01) |
| H04B 5/02 | (2006.01) |
| H04B 13/00 | (2006.01) |
| G06F 19/00 | (2018.01) |
| A61B 5/00 | (2006.01) |

(52) U.S. Cl.
CPC ......... H04R 25/60 (2013.01); G06F 19/3481 (2013.01); G08C 17/04 (2013.01); H04B 5/0012 (2013.01); H04B 5/0031 (2013.01); H04B 5/0081 (2013.01); H04B 5/0093 (2013.01); H04B 5/02 (2013.01); H04B 13/005 (2013.01); H04R 25/554 (2013.01); H04R 25/558 (2013.01); A61B 5/002 (2013.01)

(58) Field of Classification Search
CPC .. H04R 25/558; H04R 25/554; H04R 25/505; H04R 25/552; H04B 13/005; H04B 5/0012; H04B 5/0031; H04B 5/0037; A61B 5/0028; G08C 17/04; G08C 17/06
See application file for complete search history.

(56) References Cited

U.S. PATENT DOCUMENTS

| 3,766,476 A | 10/1973 | Silitch |
| 4,334,315 A | 6/1982 | Ono |
| 4,692,743 A | 9/1987 | Holden |
| 5,673,054 A | 9/1997 | Hama |
| 5,708,732 A | 1/1998 | Merhav et al. |
| 5,907,522 A | 5/1999 | Teodoridis |
| 5,914,701 A | 6/1999 | Gersheneld |

(Continued)

FOREIGN PATENT DOCUMENTS

| CN | 102013895 A | 4/2011 |
| CN | 102570000 A | 7/2012 |

(Continued)

OTHER PUBLICATIONS

Kado et al., RedTacton Near-Body Electric-Field Communications Technology and Its Applications, Mar. 3, 2010, NTT Technical Review, vol. 8 No. 3, pp. 1-6.*

(Continued)

*Primary Examiner* — Fan Tsang
*Assistant Examiner* — Angelica M McKinney (57) ABSTRACT

Consistent with an example embodiment there is an electromagnetic induction field communication system, illustratively, for communicating on or around the body. Two transceivers (or receiver and transmitter) contain coils and capacitors suitable for generating an electromagnetic induction field surrounding the body and are capable of communicating therebetween.

19 Claims, 4 Drawing Sheets

(56) References Cited

U.S. PATENT DOCUMENTS

| | | |
|---|---|---|
| 5,926,573 A | 7/1999 | Kim et al. |
| 5,948,006 A | 9/1999 | Mann |
| 6,104,913 A | 8/2000 | McAllister |
| 6,211,799 B1* | 4/2001 | Post .................... A61B 5/0028 341/33 |
| 6,223,018 B1* | 4/2001 | Fukumoto ............... H04B 5/00 379/55.1 |
| 6,275,737 B1 | 8/2001 | Mann |
| 6,424,820 B1 | 7/2002 | Burdick et al. |
| 6,754,472 B1 | 6/2004 | Williams |
| 6,816,600 B1 | 11/2004 | Jakob |
| 7,142,681 B2 | 11/2006 | Kortekaas |
| 7,171,177 B2 | 1/2007 | Park et al. |
| 7,206,423 B1* | 4/2007 | Feng .................... H04B 13/005 381/312 |
| 7,254,246 B2 | 8/2007 | Jakob |
| 7,509,092 B2* | 3/2009 | Ishibashi ............. H04B 5/0012 340/5.52 |
| 7,664,476 B2 | 2/2010 | Yanagida |
| 7,684,769 B2 | 3/2010 | Song et al. |
| 7,783,067 B1 | 8/2010 | Frerking |
| 7,796,943 B2 | 9/2010 | Levan |
| 7,907,057 B2 | 3/2011 | Schaffler et al. |
| 8,005,547 B2 | 8/2011 | Forsberg |
| 8,237,622 B2 | 8/2012 | Furumura et al. |
| 8,265,554 B2 | 9/2012 | Hwang |
| 8,280,302 B2 | 10/2012 | Kubono |
| 8,401,470 B2* | 3/2013 | Kroekenstoel ........... H04B 1/04 333/175 |
| 8,452,234 B2 | 5/2013 | Hasegawa et al. |
| 8,509,689 B2 | 8/2013 | Nakamura et al. |
| 8,526,879 B2 | 9/2013 | Kristiansen |
| 8,606,177 B2 | 12/2013 | Hwang |
| 8,644,542 B2 | 2/2014 | Klemenz |
| 8,797,148 B2 | 8/2014 | Kato et al. |
| 8,829,725 B2 | 9/2014 | Urano |
| 8,878,735 B2 | 11/2014 | Kvist et al. |
| 8,892,055 B2 | 11/2014 | Gasperi |
| 8,909,966 B2 | 12/2014 | Furukawa |
| 9,019,131 B2 | 4/2015 | Kim |
| 9,024,725 B2 | 5/2015 | Ikemoto |
| 9,083,391 B2 | 7/2015 | Teggatz |
| 9,130,273 B2 | 9/2015 | Kataoka |
| 9,197,986 B1 | 11/2015 | Kerselaers et al. |
| 9,314,381 B2 | 4/2016 | Curran et al. |
| 9,455,771 B2 | 9/2016 | Dobyns |
| 9,647,462 B2 | 5/2017 | Angst et al. |
| 2002/0003503 A1 | 1/2002 | Justice |
| 2002/0181579 A1 | 12/2002 | Vetro et al. |
| 2004/0023216 A1 | 2/2004 | Lu et al. |
| 2004/0027296 A1* | 2/2004 | Gerber .................. H01Q 1/243 343/702 |
| 2004/0138723 A1* | 7/2004 | Malick ................ H04R 25/552 607/57 |
| 2005/0058201 A1 | 3/2005 | Fernandes |
| 2006/0008038 A1 | 1/2006 | Song et al. |
| 2006/0114993 A1 | 6/2006 | Xiong et al. |
| 2006/0134918 A1 | 6/2006 | Fuji et al. |
| 2006/0215919 A1 | 9/2006 | Srinivasan |
| 2006/0233258 A1 | 10/2006 | Holcomb |
| 2006/0252371 A1 | 11/2006 | Toshiharu |
| 2007/0058713 A1 | 3/2007 | Shen et al. |
| 2007/0116308 A1 | 5/2007 | Zurek et al. |
| 2007/0190940 A1* | 8/2007 | Lee et al. .................. 455/41.2 |
| 2007/0291970 A1 | 12/2007 | Nikles |
| 2008/0182517 A1* | 7/2008 | Rass .................... H04B 5/00 455/41.3 |
| 2008/0186241 A1 | 8/2008 | Christensen |
| 2008/0261523 A1* | 10/2008 | Kubono ............... H04B 5/0012 455/41.1 |
| 2008/0262376 A1 | 10/2008 | Price |
| 2008/0267436 A1* | 10/2008 | Kerselaers ............... H01Q 7/00 381/315 |
| 2009/0041241 A1 | 2/2009 | Dobyns et al. |
| 2009/0067653 A1* | 3/2009 | Meskens ............. H04R 25/552 381/315 |
| 2009/0202084 A1 | 8/2009 | Joeng et al. |
| 2009/0238279 A1 | 9/2009 | Tu et al. |
| 2009/0315787 A1 | 12/2009 | Schatzle |
| 2009/0322540 A1 | 12/2009 | Richardson et al. |
| 2010/0036773 A1* | 2/2010 | Bennett ............. G06Q 20/3674 705/67 |
| 2010/0136905 A1 | 6/2010 | Kristiansen |
| 2010/0311326 A1 | 12/2010 | Klabunde et al. |
| 2011/0029041 A1 | 2/2011 | Wiskerke |
| 2011/0046730 A1 | 2/2011 | Meskens |
| 2011/0137649 A1 | 6/2011 | Rasmussen |
| 2011/0196452 A1 | 8/2011 | Forsell |
| 2011/0248673 A1 | 10/2011 | Aerts et al. |
| 2011/0250837 A1 | 10/2011 | Hwang et al. |
| 2011/0255702 A1 | 10/2011 | Jensen |
| 2011/0300801 A1 | 12/2011 | Kerselaers |
| 2012/0032778 A1* | 2/2012 | Nakano et al. ............ 340/5.52 |
| 2012/0306714 A1 | 12/2012 | Yosui et al. |
| 2013/0002517 A1 | 1/2013 | Pascolini et al. |
| 2013/0113662 A1 | 5/2013 | Kato et al. |
| 2013/0148828 A1 | 6/2013 | Fort |
| 2013/0171933 A1 | 7/2013 | Rofougaran |
| 2013/0278470 A1 | 10/2013 | Kataoka |
| 2013/0308805 A1 | 11/2013 | Ozden |
| 2013/0339025 A1 | 12/2013 | Suhami |
| 2014/0008446 A1 | 1/2014 | Carr |
| 2014/0023216 A1* | 1/2014 | Solum .................. H04R 25/554 381/315 |
| 2014/0049440 A1 | 2/2014 | Ueki et al. |
| 2014/0062212 A1 | 3/2014 | Sun et al. |
| 2014/0184462 A1 | 7/2014 | Kuniaki |
| 2014/0213184 A1* | 7/2014 | Matsubara ........... H04B 5/0031 455/41.1 |
| 2014/0241555 A1 | 8/2014 | Terlizzi |
| 2014/0315486 A1 | 10/2014 | Broyde et al. |
| 2014/0320369 A1 | 10/2014 | Azenui et al. |
| 2014/0340032 A1 | 11/2014 | Curtis |
| 2015/0001956 A1 | 1/2015 | Saen |
| 2015/0028690 A1 | 1/2015 | Sako |
| 2015/0038075 A1 | 2/2015 | Kataoka |
| 2015/0038864 A1* | 2/2015 | Kataoka ............... A61B 5/0402 600/509 |
| 2015/0048985 A1 | 2/2015 | Park et al. |
| 2015/0061587 A1 | 3/2015 | Bruechmann |
| 2015/0079902 A1 | 3/2015 | Dhayni |
| 2015/0092962 A1 | 4/2015 | Amento |
| 2015/0097442 A1 | 4/2015 | Muurinen |
| 2015/0130465 A1 | 5/2015 | Wiggins et al. |
| 2015/0318603 A1 | 11/2015 | Kerselaers et al. |
| 2015/0318613 A1 | 11/2015 | Kerselaers et al. |
| 2015/0318896 A1 | 11/2015 | Kerselaers et al. |
| 2015/0318932 A1 | 11/2015 | Kerselaers et al. |
| 2015/0351292 A1 | 12/2015 | Chang et al. |
| 2016/0189860 A1 | 6/2016 | Konanur et al. |
| 2017/0125883 A1 | 5/2017 | Tenno |

FOREIGN PATENT DOCUMENTS

| | | |
|---|---|---|
| CN | 103024621 A1 | 4/2013 |
| KR | 101584555 B1 | 1/2016 |
| WO | WO03030991 A1 | 4/2003 |
| WO | WO2013183575 | 12/2013 |

OTHER PUBLICATIONS

Kado et al., RedTacton Near-Body Electric-Field Communications Technology and Its Applications, Mar. 3, 2010, NTT Technical Review, vol. 8, No. 3, p. 1-6.*

Zimmerman, Personal Area Networks (PAN) Near-Filed Intra-Body Communication, 1995, Massachusets Institute of Technology, p. 36.*

T.G. Zimmerman, Personal Area Networks: Near-Field Intrabody Communication, 1996, IBM System Journal, vol. 35, pp. 609-617.*

Kado, Yuichi et al; "RedTacton Near-body Electric-field Communications Technology and Its Applications"; NTT Technical Review, (56) References Cited

OTHER PUBLICATIONS vol. 8, No. 3; NTT Microsystem Integration Laboratories, Atsugi-shi, JP; 6 pages (Mar. 2010).
Cho, et al., A Planar MICS Band Antenna Combined with a Body Channel Communication Electrode for Body Sensor Network.
Shinagawa, et al., A Near-Field-Sensing Transceiver for Intra-body Communication Based on the Electro-Optic Effect.
International Search Report dated Jul. 9, 2015 for International Application No. PCT/EP2015/058071.
International Search Report dated Jul. 13, 2015 for International Application No. PCT/EP2015/058044.
International Search Report dated Jul. 17, 2015 for International Application No. PCT/EP2015/058052.
Non Final Office Action dated Jun. 29, 2016 for U.S. Appl. No. 14/551,988, 23 pages.
Notice of Allowance dated Jul. 21, 2015 for U.S. Appl. No. 14/302,791, 9 pages.
U.S. Appl. No. 14/551,988, filed Nov. 24, 2014, entitled "Electromagnetic Field Induction for Inter-Body and Transverse Body Communication".
European Search Report dated Aug. 31, 2015 EP 15164678, 6 pages.
Final Office Action dated Mar. 7, 2016 for U.S. Appl. No. 14/576,030, 13 pages.
Non-Final Office Action dated Oct. 5, 2015 for U.S. Appl. No. 14/576,030, 17 pages.
European Search Report dated Aug. 31, 2015 for EP 15164622, 6 pages.
Final Office Action dated Feb. 25, 2016 for U.S. Appl. No. 14/576,583, 13 pages.
Non-Final Office Action dated Sep. 21, 2015 for U.S. Appl. No. 14/576,583, 17 pages.
European Search Report dated Aug. 31, 2015 for EP 15164621, 8 pages.
Non-Final Office Action dated Oct. 5, 2015 for U.S. Appl. No. 14/569,024, 14 pages.
Final Office Action dated Feb. 25, 2016 for U.S. Appl. No. 14/569,024, 13 pages.
Non-Final Office Action dated Oct. 5, 2015 for U.S. Appl. No. 14/575,865, 17 pages.
Final Office Action dated Mar. 4, 2016 for U.S. Appl. No. 14/575,865, 14 pages.
European Search Report dated Aug. 31, 2015 for EP 15164610, 6 pages.
U.S. Appl. No. 14/836,681, filed Aug. 26, 2015, entitled "Antenna System".
U.S. Appl. No. 15/146,665, filed May 4, 2016, entitled "Near-Field Electromagnetic Induction (NFEMI) Antenna".
Chandrasekar, K., "Inductively Coupled Connectors and Sockets for Multi-Gb/s Pulse Signaling," IEEE Transactions on Advanced Packaging, vol. 31, No. 4; Nov. 1, 2008, pp. 749-758.
Ohishi, T. et al., "Novel Pair Electrode With Coils Sensing Magnetic Energy on Human Body Surface for Intrabody Communication," IEEE International Symposium on Antennas and Propagation (ISAP); Oct. 29, 2012; pp. 203-206.
Tounsi, F. et al. "Electromagnetic Modeling of an Integrated Micromachined Inductive Microphone," IEEE 4th International Conference on Design and Technology of Integrated Systems in Nanoscale Era; Apr. 6, 2009; pp. 38-43.
Non-Final Office Action for U.S. Appl. No. 14/576,583, dated Nov. 3, 2016, 33 pages.
Non-Final Office Action dated Jan. 3, 2017 for U.S. Appl. No. 14/576,030, 39 pages.
Non-Final Office Action dated Jan. 19, 2017 for U.S. Appl. No. 14/575,865, 45 pages.
Non-Final Office Action dated Jan. 19, 2017 for U.S. Appl. No. 14/551,988, 21 pages.
Non-Final Office Action dated Jan. 25, 2017 for U.S. Appl. No. 14/569,024, 51 pages.
Final Office Action dated Aug. 9, 2017 for U.S. Appl. No. 14/569,024, 52 pages.
Notice of Allowance dated Jun. 7, 2017 for U.S. Appl. No. 14/551,988, 25 pages.
Notice of Allowance dated Jun. 14, 2017 for U.S. Appl. No. 14/836,681, 14 pages.
Notice of Allowance dated Jun. 27, 2017 for U.S. Appl. No. 14/576,030 30 pages.
Notice of Allowance dated Jun. 21, 2017 for U.S. Appl. No. 14/576,583 34 pages.
Final Office Action dated Jul. 27, 2017 for U.S. Appl. No. 14/575,865, 56 pages.
Notice of Allowance dated Mar. 13, 2018 for U.S. Appl. No. 14/569,024, 15 pages.
Notice of Allowance dated Mar. 22, 2018 for U.S. Appl. No. 14/575,865, 24 pages.
Non Final Office Action dated May 24, 2018 for U.S. Appl. No. 15/146,665, 96 pages.

\* cited by examiner

ELECTROMAGNETIC INDUCTION FIELD COMMUNICATION

FIELD

This disclosure relates to an apparatus and method of communicating using electromagnetic fields.

BACKGROUND

There exist a variety of wireless systems which, illustratively, are used for short range distance communication. Some systems are used for communication around the human body; other systems may be used for communication in or around other objects. For example, currently RF based hearing aids are considered for wireless communication. Often such hearing aid systems operate in the 2.5 GHz ISM band. Such systems feature propagation by means of transverse waves, the magnetic and electric fields being in phase and covering a relatively large range of perhaps 30 meters. The large range may cause problems in terms of security of the communication content and may cause interference. Furthermore, because of their relatively high frequency of operation, such systems are heavily influenced by the human body.

Somewhat more conventional hearing aids employ magnetic field induction as a wireless communication method. Unfortunately, magnetic field induction based wireless systems have a limited range if the antenna is comparatively small, such as would be required in a hearing aid. Not all parts of the human body can be reached with magnetic field induction-based systems with small antennas. Consequently, it can be difficult to provide communication between a hearing aid and a hand-held control using such systems.

Figure 1:
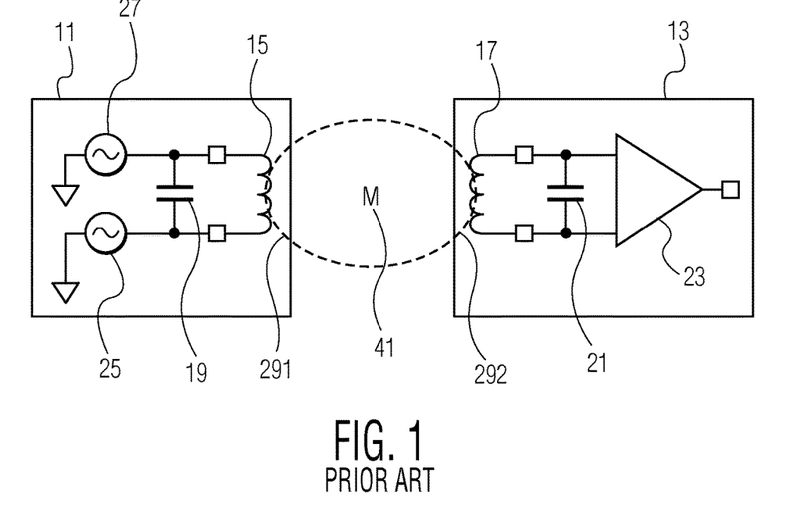
FIG. 1 is a circuit diagram illustrative of a communication system which uses magnetic field induction.

FIG. 1 is a circuit diagram of a prior art wireless communication system utilizing magnetic field induction. Reference numeral 11 denotes a transmitter which may illustratively be contained in a hearing aid designed for positioning proximate to or into one ear. Reference numeral 13 denotes a receiver which may illustratively be contained in a hearing aid designed for positioning proximate to or into the other ear. It is desired to have communication between the two hearing aids so that signals transmitted from transmitter 11 and received by receiver 13 may be processed (by processing circuitry near or inside the receiver) to enhance the user's hearing experience and make that experience more natural. In certain implementations, bidirectional communication is also possible in which transmitter 11 and receiver 13 are transceivers. Transmitter 11 contains sources 25 and 27 and a resonant circuit which includes coil 15 and capacitor 19. Magnetic field 291, also denoted as H1, is generated via coil 15. Receiver 13 contains a resonant circuit formed by coil 17 and capacitor 21 and a low noise amplifier 23. The resonant circuit of receiver 13 resonates at the same frequency as the resonant circuit of transmitter 11. A voltage is induced in coil 17 by magnetic field 292, also denoted as H2, thereby creating a signal communication path. The mutual coupling factor between coils 15 and 17 is denoted by M, reference numeral 41.

SUMMARY

Although the appended claims are directed to particular combinations of features, it should be understood that the scope of the disclosure also includes any novel feature or novel combination of features disclosed herein.

Features which are described in the context of separate embodiments may also be provided in combination in a single embodiment. Conversely, various features which are, for brevity, described in the context of a single embodiment, may also be provided separately or in any suitable subcombination.

Comprehended are a communication system having a transmitter having a coil, a capacitor which has first and second plates, the first plate being connectable to a living body; the second plate being configured to be exposed to the environment; the transmitter being capable of generating a combination of magnetic and electric induction fields; and a receiver having a coil, a capacitor which has first and second plates, the first plate of the receiver being connectable to a living body; and the second plate being connectable to the environment; and further, there being no galvanic connection between the transmitter and ground or between the receiver and ground. Further comprehended is a tuning capacitor in the transmitter. In addition, there is comprehended a tuning capacitor in the receiver. Also, the transmitter may be a transceiver and the receiver may be a transceiver. In addition, the transmitter may be included in a hearing aid and the receiver may be included in a hearing aid. In further embodiments, the transmitter and receiver are tuned in accordance with the body's capacitance to effect communication therebetween. In addition, there may be included a wireless control unit adapted to be held by the hand, such control unit communicating with their the receiver or transmitter via the electromagnetic induction field. Furthermore, there is comprehended a control unit having a capacitor with two plates, one the plates being adapted for contact with the body. In addition, the control unit may have a display.

DETAILED DESCRIPTION OF EMBODIMENTS

Figure 2:
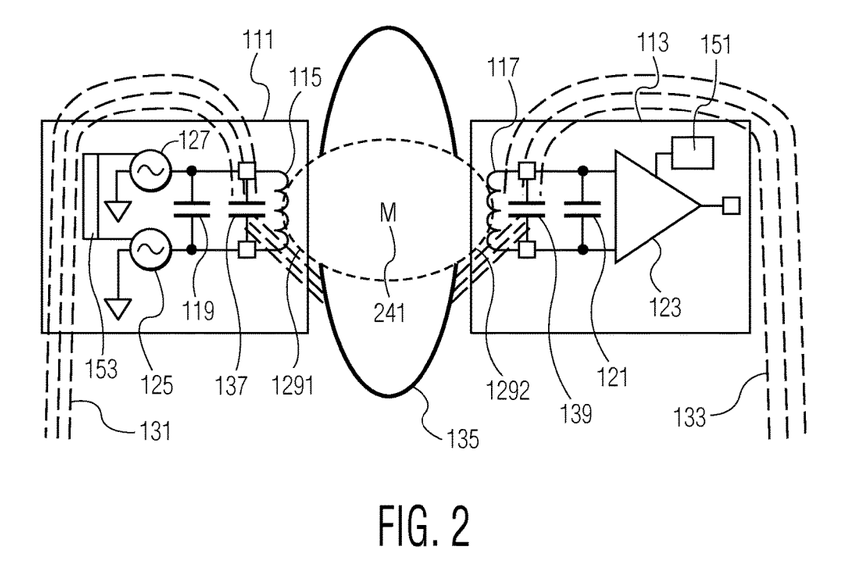
FIG. 2 is a circuit diagram of an illustrative embodiment of this disclosure.

FIG. 2 shows an illustrative embodiment. Depicted are transmitter 111 and receiver 113. Communication between transmitter 111 and receiver 113 is accomplished via a combination of electric field and magnetic field as will be further described. Magnetic field 1291 is generated by current through coil 115. An electric field 131 can be generated by a voltage on coupling capacitor 137. Coupling capacitor 137 has a first conducting plate coupled to the human body 135 and a second conducting plate coupled to the environment as will be further illustrated below.

Magnetic field 1291, which may be denoted by H3, and electric field 131 can be generated by the same voltage using sources 125 and 127. In this illustrative embodiment the sources 125 and 127 are generating a balanced voltage across the coil 115. However the voltage across the coil 115 can also be unbalanced and in this case only one source is required.

Magnetic field 1292, which may be denoted by H4, and electric field 133 (which has a different amplitude than electric field 131) can be received at a receiver 113 positioned at another place near the human body (perhaps in the other ear) by means of a coil 117 and a coupling capacitor 139. Coupling capacitor 139 has a first conducting plate coupled to the human body 135 and a second conducting plate coupled to the environment as will be further illustrated in FIG. 3. The mutual coupling factor between coils 115 and 117 is denoted by M, reference numeral 241.

Figure 3:
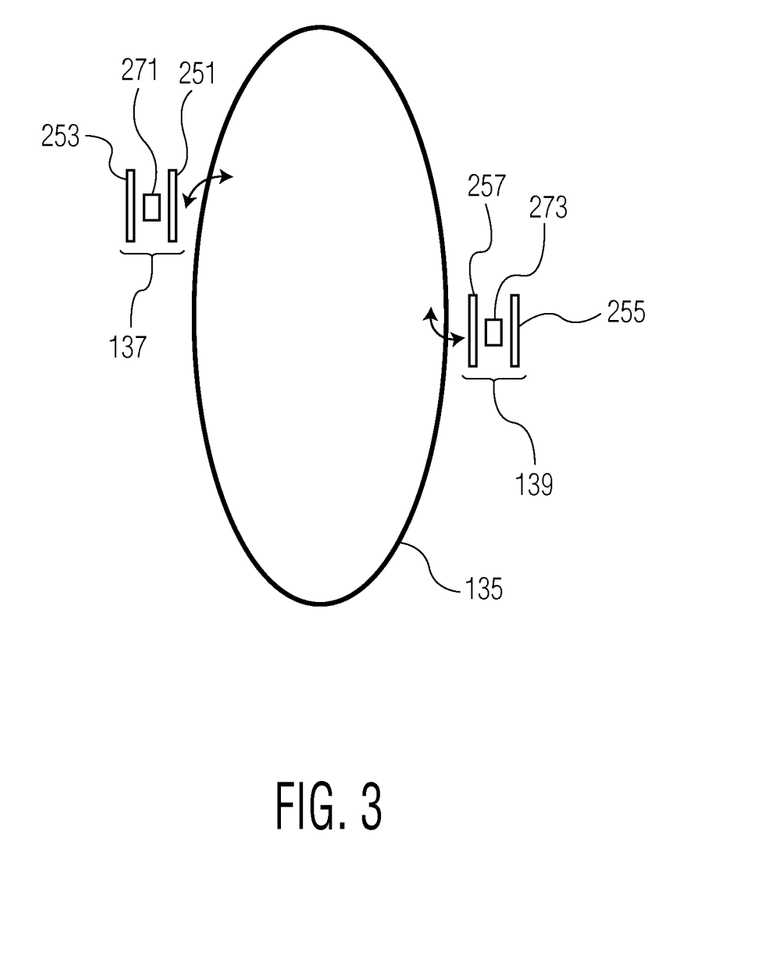
FIG. 3 is a diagram of an illustrative embodiment of this disclosure.

In FIG. 3, there are depicted capacitors 137 and 139 positioned near human body 135. Capacitors 137 and 139 may, illustratively, be portions of a hearing aid. Both capacitors can be formed by two conductive plates. For example, capacitor 137 may have plates 251 and 253, each on an opposite side of the hearing aid. Plate 251 is close to or in contact with the head of human body 135, while plate 253, which is less close to and not in contact with the head of human body 135 (possibly on the other side of the hearing aid) is exposed (i.e. connected) to the environment. Similarly, capacitor 139 has plates 257 and 255. Plate 257 is close to or in contact with the head of human body 135, while plate 255 is less close to and not in contact with the head of human body 135 is exposed (i.e. connected) to the environment. Plates 251, 253, 257, and 255 are made from conductive material, illustratively metal. The electronics required for hearing aid function, denoted by reference numerals 271 and 273, may be located between the respective plates of the two capacitors (e.g. between plates 251 and 253). In general, plates 251, 253, 257, and 255 may have a variety of shapes and may be surrounded by dielectric material as long as the overall structure, 137 and 139 performs a capacitive function. In general, the dimensions of capacitors 137 and 139 should be small relative to the wavelength of operation. Capacitors 119 and 121 are provided to resonate their respective circuits at the required operational frequency. By way of an example embodiment, if capacitors 137 and 139 are approximately 10 pF in value (which is somewhat defined by coupling capacitor design), while coils 115 and 117 are be approximately 3.7 µH, then some extra capacitance may be required to tune the circuit to the desired operational frequency, for example 10.6 MHz. Consequently the values of capacitors 119 and 121 are approximately 50.96 pF. In an embodiment, capacitors 119 and 121 are a capacitor bank which may be integrated into an RF integrated circuit that is adjustable to resonate at the required frequency. The adjustability compensates for the added capacitance due to the human body.

In operation, illustratively, coil 115 generates a magnetic near field 1291 whose field lines are sufficient to reach coil 117 and a voltage is induced in coil 117 by magnetic field 1292. Capacitor 137 generates an electric near field 131 between the skin of the human user and the environment. Both the magnetic near field 1292 and electric near field 133 are capable of being sensed by a similar circuit in receiver 113. There is no galvanic connection between transmitter 111 and ground. There is no galvanic connection between receiver 113 and ground.

FIG. 2 shows an illustrative embodiment of a transmitter and receiver that allows uni-directional communication. In another embodiment, both 111 and 117 may be also transceivers and bi-directional communication is thus made possible.

Not illustrated in detail are driving circuitry, signal processing circuitry, microphones, control circuitry, etc., although such items may be viewed as embodied in blocks denoted by reference numerals 153 or 151 in FIG. 2 or blocks 271 or 273 in FIG. 3.

Figure 4:
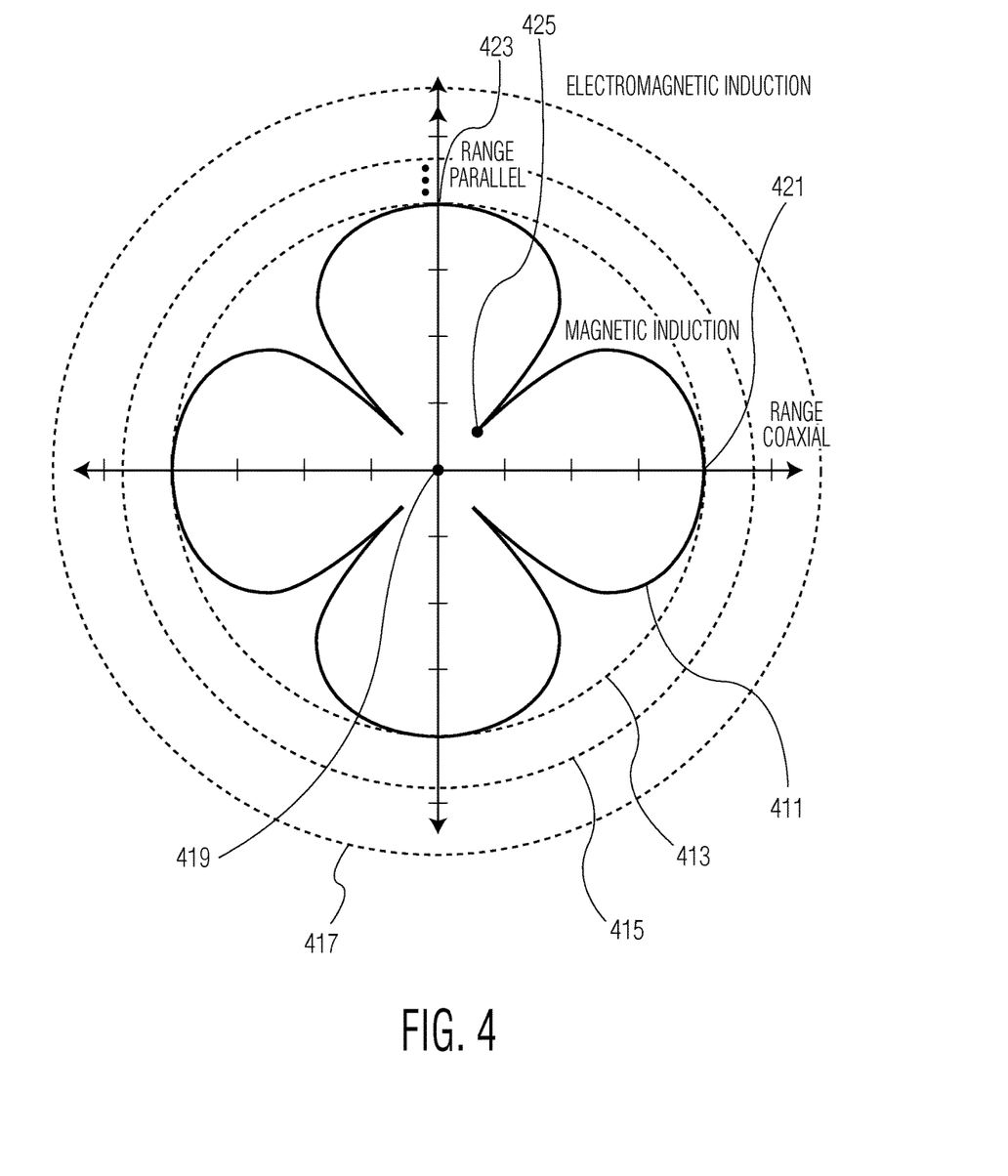
FIG. 4 is a diagram of a communication system which uses magnetic field induction; and that of a communication system which uses the method of this disclosure.

FIG. 4 is a diagram illustrating comparative ranges of a communication system which uses magnetic field induction and a communication system which uses the method of this disclosure. In FIG. 4, the horizontal axis indicates directivity when coils 115 and 117 are coaxial; the vertical axis indicates directivity when coils 115 and 117 are parallel. The directivity in case of a link using the magnetic field induction method is illustrated by line 411. It will be noted that the range drops significantly when moving from the case where both coils are coaxial to the case where coils are parallel. Using the diagram of FIG. 4, if the transmit coil 115 of FIG. 2 were located at the origin 419 of FIG. 4, one can see that the receiver coil 117 can be placed in either location 421 or 423 (which correspond, respectively, to a coaxial orientation with respect to the transmitter coil 115 or a parallel orientation with respect to transmitter coil 115) and best-case detection of the magnetic field generated by transmit coil 115 will be achieved. However, if the receiver coil 117 is positioned along a line which is oriented at forty five degrees between locations 421 and 423, (i.e. at location 425), the receiver coil must be placed substantially closer to the transmitter coil 115 for adequate detection to occur. The disclosed embodiment, however exhibits a more omnidirectional range profile and possibly greater range. The omnidirectional profile and possibly greater range in case of a link using electromagnetic induction fields facilitate more robust communication.

Figure 6:
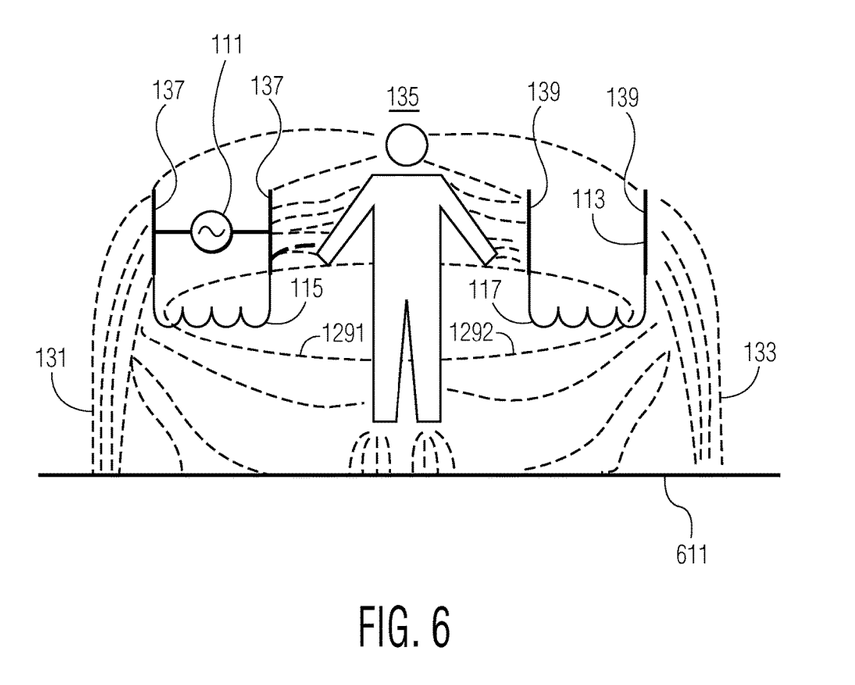
FIG. 6 depicts a front view of a human body with an illustrative embodiment.

FIG. 6 is a front view of a human body with an illustrative embodiment. Depicted are a human body 135; transmitter 111, with capacitor 137; and receiver 113 with capacitor 139. Also depicted is electric field 131 and 133 (which as can be appreciated from a view of FIG. 4 are parts of the same field). Transmitter 111 and receiver 113 are spaced apart from human body 135 by an exaggerated distance so that the electric field lines may be shown. It will be noted that there is no galvanic connection between transmitter 111 and ground and there is also no galvanic connection between receiver 113 and ground. It will be noted that the electric field lines 131 and 133 extend down the length of the human body 135. Furthermore as a view of FIG. 4 has illustrated, the electromagnetic field lines extend circumferentially around the human body 135. Consequently the electromagnetic field may be utilized to enhance and make more reliable communication between transmitter 111 and receiver 113. In the embodiments discussed, the coils and coupling capacitors are so small that (i.e. less than about 5% of the wavelength of the electric 131 and magnetic 1291 fields, that there is not significant generation of undesired transverse radiating waves.

In an embodiment, coils 115 and 117 are unscreened and smaller (ideally much smaller) than the chosen wavelength of operation. The capacitors 137 and 139 each have one conducting surface, i.e. 251 and 257 in FIG. 3, which is close to or in contact with a body, illustratively, a human body 135. The opposing surfaces, i.e. plates 253 and 255 of FIG. 3 are closer to the environment than the human body 135, and the size of the plates are smaller (ideally much smaller) than the chosen wavelength of operation. Plates 253 and 251 are preferably parallel and have the same shape, but it is also permissible that the plates are of different size and only partially parallel (i.e. somewhat non-parallel) or side by side. Similarly for plates 257 and 255.

Figure 5:
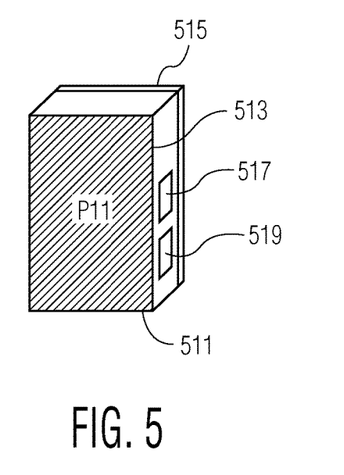
FIG. 5 depicts a control/display unit in accordance with another embodiment.

In another embodiment, there may be a separate control and/or display unit. FIG. 5. Depicts a control and/or display unit 511. Control and/or display unit 511 has two plates 513 and 515 on opposite sides. Control and/or display unit 511 may be held in the hand of a user. One of the plates, 513 or 515 will be held more securely in the hand than the other and will therefore be more strongly coupled to the user's body, while the other plate will have a somewhat stronger coupling to the environment. Control and/or display unit 511 is capable of communicating with transmitter 111 or receiver 113. Illustratively, control and/or display unit may, in combination, or individually, provide: volume control; noise reduction control; human body parameters such as heart rate, and other items such as physical parameters monitored around the body. Operation of the control and/or display unit is facilitated by the electromagnetic field 1291 and 131. In an embodiment, dimensioning and parallelism are similar to that described for plates 253 and 255 above. Control and/or display unit may have a display, and internal circuitry, 591, similar to either transmitter 111 or receiver 113 (or may have internal circuitry which is a transceiver as previously described).

Various exemplary embodiments are described in reference to specific illustrative examples. The illustrative examples are selected to assist a person of ordinary skill in the art to form a clear understanding of, and to practice the various embodiments. However, the scope of systems, structures and devices that may be constructed to have one or more of the embodiments, and the scope of methods that may be implemented according to one or more of the embodiments, are in no way confined to the specific illustrative examples that have been presented. On the contrary, as will be readily recognized by persons of ordinary skill in the relevant arts based on this description, many other configurations, arrangements, and methods according to the various embodiments may be implemented.

To the extent positional designations such as top, bottom, upper, lower have been used in describing this invention, it will be appreciated that those designations are given with reference to the corresponding drawings, and that if the orientation of the device changes during manufacturing or operation, other positional relationships may apply instead. As described above, those positional relationships are described for clarity, not limitation.

The present invention has been described with respect to particular embodiments and with reference to certain drawings, but the invention is not limited thereto, but rather, is set forth only by the claims. The drawings described are only schematic and are non-limiting. In the drawings, for illustrative purposes, the size of various elements may be exaggerated and not drawn to a particular scale. It is intended that this invention encompasses inconsequential variations in the relevant tolerances and properties of components and modes of operation thereof. Imperfect practice of the invention is intended to be covered.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present invention, the only relevant components of the device are A and B.

What is claimed is:

1. A communication system comprising:
    a transmitter located at a first position on a living body, the transmitter having:
        a first coil,
        a first capacitor having first and second plates, said first capacitor connected in parallel with said first coil, said first plate being coupled to the living body at the first position and said second plate being configured to be exposed to an environment, and
        a signal generator configured to produce a communication signal used to provide current to said first coil to generate a magnetic near field and to provide voltage to said first capacitor to generate an electric near field, wherein said electric near field is coupled to and available around the living body; and
    a receiver located at a second position on the living body distant from the first position, the receiver having:
        a second coil configured to receive said magnetic near field, wherein said magnetic near field passes through the living body, and
        a second capacitor, configured to receive said electric near field available around the living body, said second capacitor having third and fourth plates, said second capacitor connected in parallel with said second coil, said third plate being coupled to the living body at the second position and said fourth plate being exposed to the environment, there being no galvanic connection between said transmitter and ground or between said receiver and ground.

2. The communication system of claim 1, further comprising: a tuning capacitor in said transmitter configured to tune the first coil and the first capacitor to resonate at a desired operational frequency.

3. The communication system of claim 1, further comprising: a tuning capacitor in said receiver configured to tune the second coil and the second capacitor to resonate at a desired operational frequency.

4. The communication system of claim 1, wherein said transmitter is a first transceiver.

5. The communication system of claim 4, wherein the receiver is a second transceiver.

6. The communication system of claim 5, wherein the first transceiver and the second transceiver are configured for bidirectional communication.

7. The communication system of claim 1, wherein said transmitter is included in a hearing aid.

8. The communication system of claim 7, wherein the receiver is included in the hearing aid.

9. The communication system of claim 1, in which said transmitter and receiver are tuned in accordance with said living body's capacitance to effect communication.

10. The communication system of claim 1, further comprising:
    a wireless control unit configured to be held by the hand, wherein the wireless-control unit is configured to communicate with either said receiver or said transmitter via a combination of said magnetic near field and said electric near field.

11. The communication system of claim 10, wherein said wireless control unit has a third capacitor with two plates, a first plate of said two plates is configured for contact with said living body, and a second plate of said two plates is exposed to the environment.

12. The communication system of claim 10, wherein said wireless control unit has a display.

13. The communication system of claim 1, wherein the receiver is configured to sense the communication signal via both the magnetic near field and the electric near field respectively received on the second coil and the second capacitor.

14. The communication system of claim 1, wherein the signal generator comprises a first source coupled to a first terminal of the first coil and a second source coupled to a second terminal of the first coil.

15. The communication system of claim 14, wherein the first and second sources are configured to generate a balanced voltage across the first coil.

16. A communication system transceiver comprising:
a transmitter located at a first position on a living body, the transmitter comprising:
  a first coil;
  a first capacitor having a first plate and a second plate, the first capacitor connected in parallel with the first coil, the first plate placed in closer proximity to the living body than the second plate; and
  a signal generator configured to produce a generated communication signal used to provide current to the first coil to produce a generated magnetic near field and to provide voltage to the first capacitor to produce a generated electric near field; and
a receiver configured to communicate with another transceiver located at a second position on the living body distant from the first position, the receiver comprising:
  a second coil configured to sense a received magnetic near field; and
  a second capacitor having a first plate and a second plate, the second capacitor connected in parallel with the second coil, the first plate of the second capacitor placed in closer proximity to the living body than the second plate of the second capacitor, the second capacitor configured to sense a received electric near field,
wherein the transmitter further comprises a third capacitor, the third capacitor having a value selected to tune a desired operational frequency of the first coil and first capacitor based on a capacitance value of the first capacitor; and
wherein the receiver further comprises a fourth capacitor, the fourth capacitor having a value selected to tune a desired operational frequency of the second coil and second capacitor based on a capacitance value of the second capacitor.

17. The communication system transceiver of claim 16, wherein a dielectric portion of the first capacitor includes the living body.

18. The communication system transceiver of claim 17, wherein a dielectric portion of the second capacitor includes the living body.

19. The communication system transceiver of claim 16, wherein the receiver is configured to detect a received communication signal via both the received magnetic near field and the received electric near field respectively sensed by the second coil and the second capacitor.

* * * * *